(12) United States Patent
Wodnicki

(10) Patent No.: US 9,070,278 B2
(45) Date of Patent: Jun. 30, 2015

(54) FAULT TOLERANT DETECTOR ASSEMBLY

(71) Applicant: General Electric Company, Schenectady, NY (US)

(72) Inventor: Robert Gideon Wodnicki, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 238 days.

(21) Appl. No.: 13/730,806

(22) Filed: Dec. 28, 2012

(65) Prior Publication Data

US 2014/0184383 A1 Jul. 3, 2014

(51) Int. Cl.
*G08C 19/00* (2006.01)
*H04N 9/64* (2006.01)

(52) U.S. Cl.
CPC ...................................... *G08C 19/00* (2013.01)

(58) Field of Classification Search
CPC ....................................................... G08C 25/02
See application file for complete search history.

(56) References Cited

U.S. PATENT DOCUMENTS

| | | | | |
|---|---|---|---|---|
| 5,367,156 | A * | 11/1994 | Domon et al. | 250/214 RC |
| 5,796,418 | A | 8/1998 | Silverbrook | |
| 5,962,846 | A * | 10/1999 | Goossen | 250/214.1 |
| 6,408,402 | B1 | 6/2002 | Norman | |
| 6,469,814 | B1 * | 10/2002 | Park et al. | 398/79 |
| 6,788,895 | B2 | 9/2004 | Trezza | |
| 8,041,003 | B2 | 10/2011 | Astley et al. | |
| 2002/0176535 | A1 * | 11/2002 | Dixon et al. | 378/62 |
| 2004/0061785 | A1 * | 4/2004 | Aufrichtig et al. | 348/207.99 |
| 2004/0095488 | A1 * | 5/2004 | Rambaldi et al. | 348/246 |
| 2005/0017746 | A1 * | 1/2005 | Matsumoto et al. | 324/763 |
| 2010/0037102 | A1 | 2/2010 | Chen et al. | |

OTHER PUBLICATIONS

Caglayan et al., "An Experimental Investigation of Software Diversity in a Fault-tolerant Avionics Application", Proceedings of the Seventh Symposium on Reliable Distributed Systems, Oct. 10-12, 1988, pp. 63-70.

Bajpai et al., "Control Laws with Hierarchical Switch Logic to Accomodate EME-induced Sensor Failures", Proceedings of the 18th Digital Avionics Systems Conference, vol. 2, 1999, pp. 10.C.3-1-10.C.3-4.

(Continued)

*Primary Examiner* — Brian Zimmerman
*Assistant Examiner* — Cal Eustaquio
(74) *Attorney, Agent, or Firm* — Seema S. Katragadda

(57) ABSTRACT

A method for forming a fault tolerant detector assembly is presented. The method includes providing a sensor array having a plurality of sensor elements, providing an electronics layer having a plurality of electronics cells, where the plurality of electronics cells corresponds to the plurality of sensor elements in the sensor array, introducing a status indicator element in each of the plurality of the electronics cells, where the status indicator element is configured to store a status of a corresponding sensor element, scanning the plurality of sensor elements in the sensor array to identify the status of the plurality of sensor elements in the sensor array, generating a functionality map based on the identified status of the plurality of sensor elements in the sensor array, and selectively programming the status indicator elements based on the functionality map to form a fault tolerant detector assembly.

25 Claims, 5 Drawing Sheets

(56) References Cited

OTHER PUBLICATIONS

Alderighi et al., "A Fault-tolerant FPGA-based Multi-stage Interconnection Network for Space Applications", Proceedings of the First IEEE International Workshop on Electronic Design, Test and Applications (DELTA•02), 2002, 5 pages.

Hereford et al., "Robust Sensor Systems using Evolvable Hardware", Proceedings of the 2004 NASA/DoD Conference on Evolution Hardware, 8 Pages.

Yan Liu & Shimon Y. Nof, "Fault-tolerant Sensor Integration for Micro Flow-sensor Arrays and Networks", Computers and Industrial Engineering, vol. 54, Issue 3, Apr. 2008, pp. 634-647.

* cited by examiner

FAULT TOLERANT DETECTOR ASSEMBLY

STATEMENT REGARDING FEDERALLY SPONSORED RESEARCH & DEVELOPMENT

This invention was made with Government support under contract number R01CA115267 awarded by the United States National Institutes of Health. The Government has certain rights in the invention.

BACKGROUND

Embodiments of the present disclosure relate to detector assemblies, and more particularly to construction of fault tolerant detector assemblies.

Sensors or transducers are devices that transform input signals of one form into output signals of a different form. Commonly used transducers include light sensors, heat sensors, and acoustic sensors. A wide variety of various applications, such as biomedical non-invasive diagnostics and non-destructive testing (NDT) of materials entail the use of sensor arrays, where the sensors are often configured in two-dimensions (that is, the X-Y plane). Moreover, applications such as medical and industrial imaging, non-destructive testing (NDT) and inspection, security, baggage scanning, and astrophysics may entail the use of sensors that encompass large areas. In the field of medical diagnostics, such as, but not limited to, X-ray, computed tomography (CT), ultrasound and mammography, it may be desirable to employ sensors that encompass large areas. For instance, in an X-ray imaging system, large area transducers may be useful to encompass the area of the X-ray detector. Also, in non-medical applications even larger arrays may be desired.

It may be noted that in a detector assembly a sensor array may be disposed in close proximity and coupled to a corresponding electronics layer/array. Moreover, defects in sensor elements in the sensor array can affect the operation of respective electronics cells and or an entire system that employs the detector assembly. Additionally, once the detector assembly is fabricated, reworking the connections between defective sensor elements and corresponding electronics cells is a challenging task. Furthermore, reflow and handling during assembly of the detector assembly may result in new defects in the sensor array that did not exist during testing of the initial bare die wafer. Consequently, it may be difficult to accurately predict and/or mitigate occurrence of such yield related issues prior to fabrication of the detector assembly. Also, locating and/or mitigating defects in the sensor array once the detector assembly is fabricated are onerous tasks.

Currently available techniques attempt to solve the issue of closely coupled sensor and electronics failures by sorting assembled devices and discarding defective arrays. Other available techniques entail examining individual components to identify defective components prior to assembly. Furthermore, certain other techniques call for identifying the defective sensor elements during an imaging procedure and data corresponding to these defective sensor elements are compensated for. However, this practice is an iterative and time-consuming process.

BRIEF DESCRIPTION

In accordance with aspects of the present disclosure, a method for forming a fault tolerant detector assembly is presented. The method includes providing a sensor array having a plurality of sensor elements. Moreover, the method includes providing an electronics layer having a plurality of electronics cells, where the plurality of electronics cells corresponds to the plurality of sensor elements in the sensor array. In addition, the method includes introducing a status indicator element in each of the plurality of the electronics cells, where the status indicator element is configured to store a status of a corresponding sensor element. The method also includes scanning the plurality of sensor elements in the sensor array to identify the status of the plurality of sensor elements in the sensor array. Furthermore, the method includes generating a functionality map based on the identified status of the plurality of sensor elements in the sensor array. Also, the method includes selectively programming the status indicator elements based on the functionality map to form a fault tolerant detector assembly.

In accordance with other aspects of the present disclosure, a fault tolerant detector assembly is presented. The assembly includes a sensor array having a plurality of sensor elements. Furthermore, the assembly includes an electronics layer having a plurality of electronics cells corresponding to the plurality of sensor elements, where each of the plurality of electronics cells includes a status indicator element configured to store a status of a corresponding sensor element.

In accordance with yet another aspect of the present disclosure, a method for forming a fault tolerant detector assembly is presented. The method includes providing a sensor array having a plurality of sensor elements. Furthermore, the method includes providing an electronics layer having a plurality of electronics cells, where the plurality of electronics cells corresponds to the plurality of sensor elements in the sensor array. The method also includes introducing a status indicator element in each of the plurality of the electronics cells, where the status indicator element is configured to store a status of a corresponding sensor element. In addition, the method includes measuring one or more of a current and a resistance in the sensor array. Moreover, the method includes estimating a number of poorly yielding sensor elements in the sensor array based on one or more of the measured current and the measured resistance in the sensor array.

In accordance with further aspects of the present disclosure, a method for forming a large area detector is presented. The method includes forming a fault tolerant detector assembly, where the method for forming the fault tolerant detector assembly includes providing a sensor array having a plurality of sensor elements, providing an electronics layer having a plurality of electronics cells, where the plurality of electronics cells correspond to the plurality of sensor elements in the sensor array, introducing a status indicator element in each of the plurality of the electronics cells, where the status indicator element is configured to store a status of a corresponding sensor element, scanning the plurality of sensor elements in the sensor array to identify the status of the plurality of sensor elements in the sensor array, generating a functionality map based on the identified status of the plurality of sensor elements in the sensor array, selectively programming the status indicator elements based on the functionality map to form a fault tolerant detector assembly. Moreover, the method includes tiling a plurality of fault tolerant detector assemblies on a support structure to form the large area detector.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

As will be described in detail hereinafter, systems and methods for forming fault tolerant detector assemblies and various embodiments of fault tolerant detector assemblies are presented. By employing the methods and detector assemblies described hereinafter, yield of the sensor arrays may be greatly enhanced.

Although, the exemplary embodiments illustrated hereinafter are described in the context of a detector assembly configured for use in an ultrasound imaging system, it will be appreciated that use of the detector assembly in other imaging systems, such as, but not limited to a computed tomography (CT) imaging system, an X-ray imaging system, a magnetic resonance (MR) imaging system, a positron emission tomography (PET) imaging system, a single photon emission computed tomography (SPECT) imaging system, a photon-counting system based on cadmium zinc telluride (CZT), cadmium telluride (CdTe), or similar direct conversion materials, and the like are also contemplated in conjunction with the present disclosure. Furthermore, use of the detector assembly in other applications such as equipment diagnostics and inspections, baggage inspections, and security applications is also envisaged.

Figure 1:
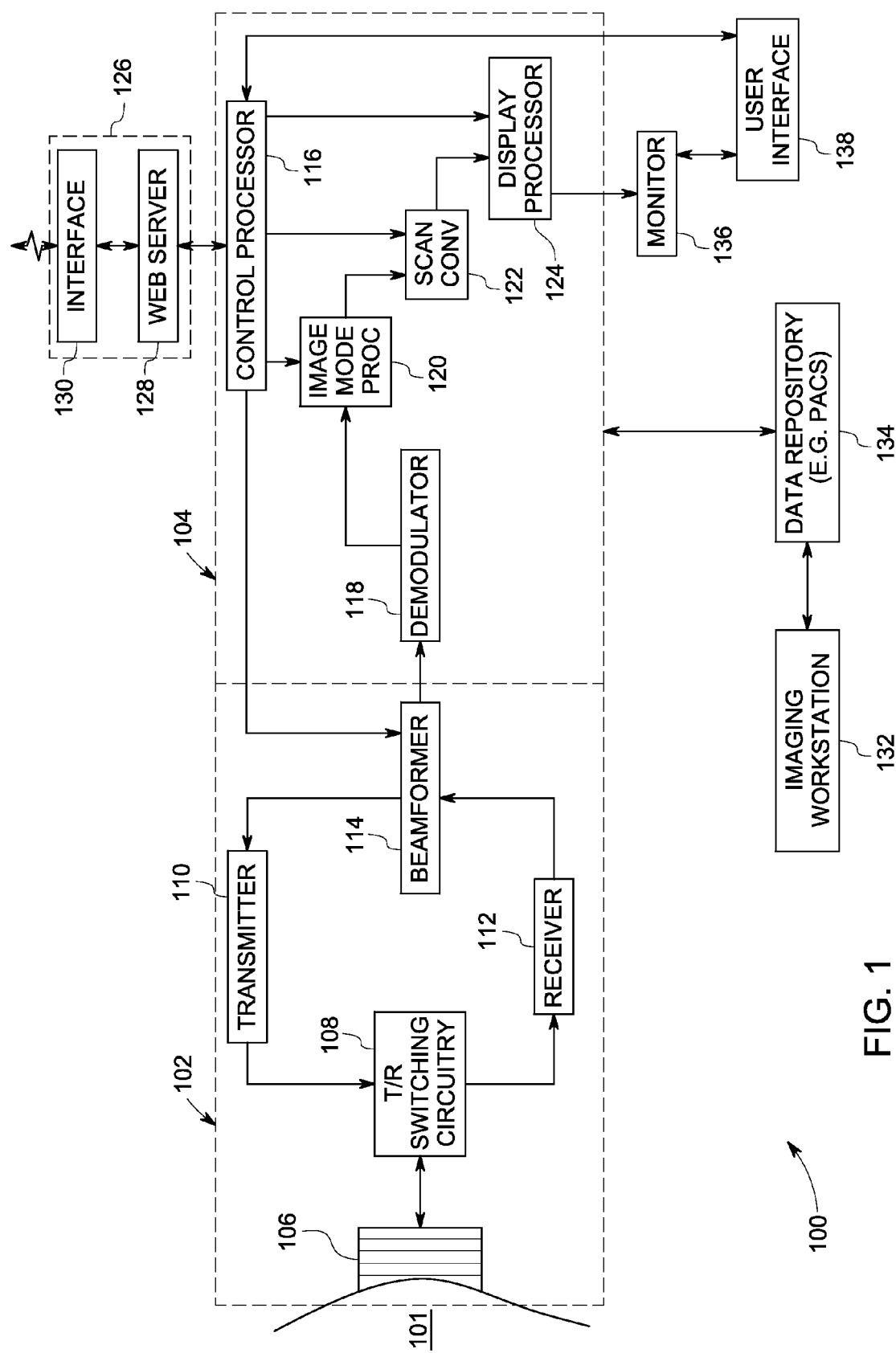
FIG. 1 is a block diagram of an imaging system in the form of an ultrasound imaging system.

Turning now to the drawings, and referring to FIG. 1, a block diagram of an embodiment of an ultrasound imaging system 100 is depicted. The ultrasound system 100 includes an acquisition subsystem 102 and a processing subsystem 104. The acquisition subsystem 102 may include a transducer assembly 106. In accordance with aspects of the present disclosure, the transducer assembly 106 may include an exemplary detector assembly (see FIG. 3) to enhance the resolution and sensitivity of the ultrasound imaging system 100.

In addition, the acquisition subsystem 102 includes transmit/receive switching circuitry 108, a transmitter 110, a receiver 112, and a beamformer 114. It may be noted that the transducer assembly 106 may be disposed in a probe, for example. Also, in certain embodiments, the transducer assembly 106 may include a plurality of transducer elements (not shown in FIG. 1) arranged in a spaced relationship to form a transducer array, such as a one-dimensional or two-dimensional transducer array, for example. Additionally, the transducer assembly 106 may include an interconnect structure (not shown in FIG. 1) configured to facilitate operatively coupling the transducer array to an external device (not shown in FIG. 1), such as, but not limited to, a cable assembly or associated electronics.

The processing subsystem 104 includes a control processor 116, a demodulator 118, an imaging mode processor 120, a scan converter 122 and a display processor 124. The display processor 124 is further coupled to a display monitor 136 for displaying images. User interface 138 interacts with the control processor 116 and the display monitor 136. The control processor 116 may also be coupled to a remote connectivity subsystem 126 including a web server 128 and a remote connectivity interface 130. The processing subsystem 104 may be further coupled to a data repository 134 configured to receive ultrasound image data. The data repository 134 interacts with an imaging workstation 132.

The aforementioned components may be dedicated hardware elements such as circuit boards with digital signal processors or may be software running on a general-purpose computer or processor such as a commercial, off-the-shelf personal computer (PC). The various components may be combined or separated according to various embodiments of the invention. Thus, those skilled in the art will appreciate that the present ultrasound imaging system 100 is provided by way of example, and the present disclosures are in no way limited by the specific system configuration.

In the acquisition subsystem 102, the transducer assembly 106 is in contact with a patient 101 (see FIG. 1). The transducer assembly 106 is coupled to the transmit/receive (T/R) switching circuitry 108. Also, the T/R switching circuitry 108 is in operative association with an output of transmitter 110 and an input of the receiver 112. The output of the receiver 112 is an input to the beamformer 114. In addition, the beamformer 114 is further coupled to the input of the transmitter 110 and to the input of the demodulator 118. The beamformer 114 is also operatively coupled to the control processor 116 as shown in FIG. 1.

In the processing subsystem 104, the output of demodulator 118 is in operative association with an input of the imaging mode processor 120. Additionally, the control processor 116 interfaces with the imaging mode processor 120, the scan converter 122 and the display processor 124. An output of the imaging mode processor 120 is coupled to an input of scan converter 122. Also, an output of the scan converter 122 is operatively coupled to an input of the display processor 124. The output of display processor 124 is coupled to the monitor 136.

The ultrasound system 100 transmits ultrasound energy into the patient 101 and receives and processes backscattered ultrasound signals from the patient 101 to create and display an image. To generate a transmitted beam of ultrasound energy, the control processor 116 communicates command data to the beamformer 114 to generate transmit parameters to create a beam of a desired shape originating from a certain point at the surface of the transducer assembly 106 at a desired steering angle. The transmit parameters are communicated from the beamformer 114 to the transmitter 110. The transmitter 110 uses the transmit parameters to properly encode transmit signals to be sent to the transducer assembly 106 through the T/R switching circuitry 108. The transmit signals are set at certain amplitudes and phases with respect to each other and are provided to individual transducer elements of the transducer assembly 106. The transmit signals excite the transducer elements to emit ultrasound waves with the same phase and amplitudes relationships. As a result, a transmitted beam of ultrasound energy is formed in the patient 101 along a scan line when the transducer assembly 106 is acoustically coupled to the patient 101 by using, for example, ultrasound gel. The process of sequentially transmitting beams to different spatial locations is known as electronic scanning.

In one embodiment, the transducer assembly 106 may be a two-way transducer. When ultrasound waves are transmitted into a patient 101, the ultrasound waves are backscattered off the tissue and blood within the patient 101. The transducer assembly 106 receives the backscattered waves at different times, depending on the distance into the tissue they return from and the angle with respect to the surface of the transducer assembly 106 at which they return. The transducer elements convert the ultrasound energy from the backscattered waves into electrical signals.

The electrical signals are then routed through the T/R switching circuitry 108 to the receiver 112. The receiver 112 amplifies and digitizes the received signals and provides other functions such as gain compensation. The digitized received signals corresponding to the backscattered waves received by each transducer element at various times preserve the amplitude and phase information of the backscattered waves.

The digitized signals are communicated to the beamformer 114. The control processor 116 communicates command data to beamformer 114. The beamformer 114 uses the command data to form a receive beam originating from a point on the surface of the transducer assembly 106 at a steering angle typically corresponding to the point and steering angle of the previous ultrasound beam transmitted along a scan line. The beamformer 114 operates on the appropriate received signals by performing time delaying and focusing, according to the instructions of the command data from the control processor 116, to create received beam signals corresponding to sample volumes along a scan line within the patient 101. Additionally, in certain other embodiments, synthetic aperture beamforming techniques may also be employed. The phase, amplitude, and timing information of the received signals from the various transducer elements are used to create the received beam signals.

The received beam signals are communicated to the processing subsystem 104. The demodulator 118 demodulates the received beam signals to create pairs of I and Q demodulated data values corresponding to sample volumes along the scan line. Demodulation is accomplished by comparing the phase and amplitude of the received beam signals to a reference frequency. The I and Q demodulated data values preserve the phase and amplitude information of the received signals.

The demodulated data is transferred to the imaging mode processor 120. The imaging mode processor 120 uses parameter estimation techniques to generate imaging parameter values from the demodulated data in scan sequence format. The imaging parameters may include parameters corresponding to various possible imaging modes such as B-mode, color velocity mode, spectral Doppler mode, and tissue velocity imaging mode, for example. The imaging parameter values are passed to the scan converter 122. The scan converter 122 processes the parameter data by performing a translation from scan sequence format to display format. The translation includes performing interpolation operations on the parameter data to create display pixel data in the display format.

The scan converted pixel data is communicated to the display processor 124 to perform any final spatial or temporal filtering of the scan converted pixel data, to apply grayscale or color to the scan converted pixel data, and to convert the digital pixel data to analog data for display on the monitor 136. The user interface 138 is coupled to the control processor 116 to allow a user to interface with the ultrasound system 100 based on the data displayed on the monitor 136.

Figure 2:
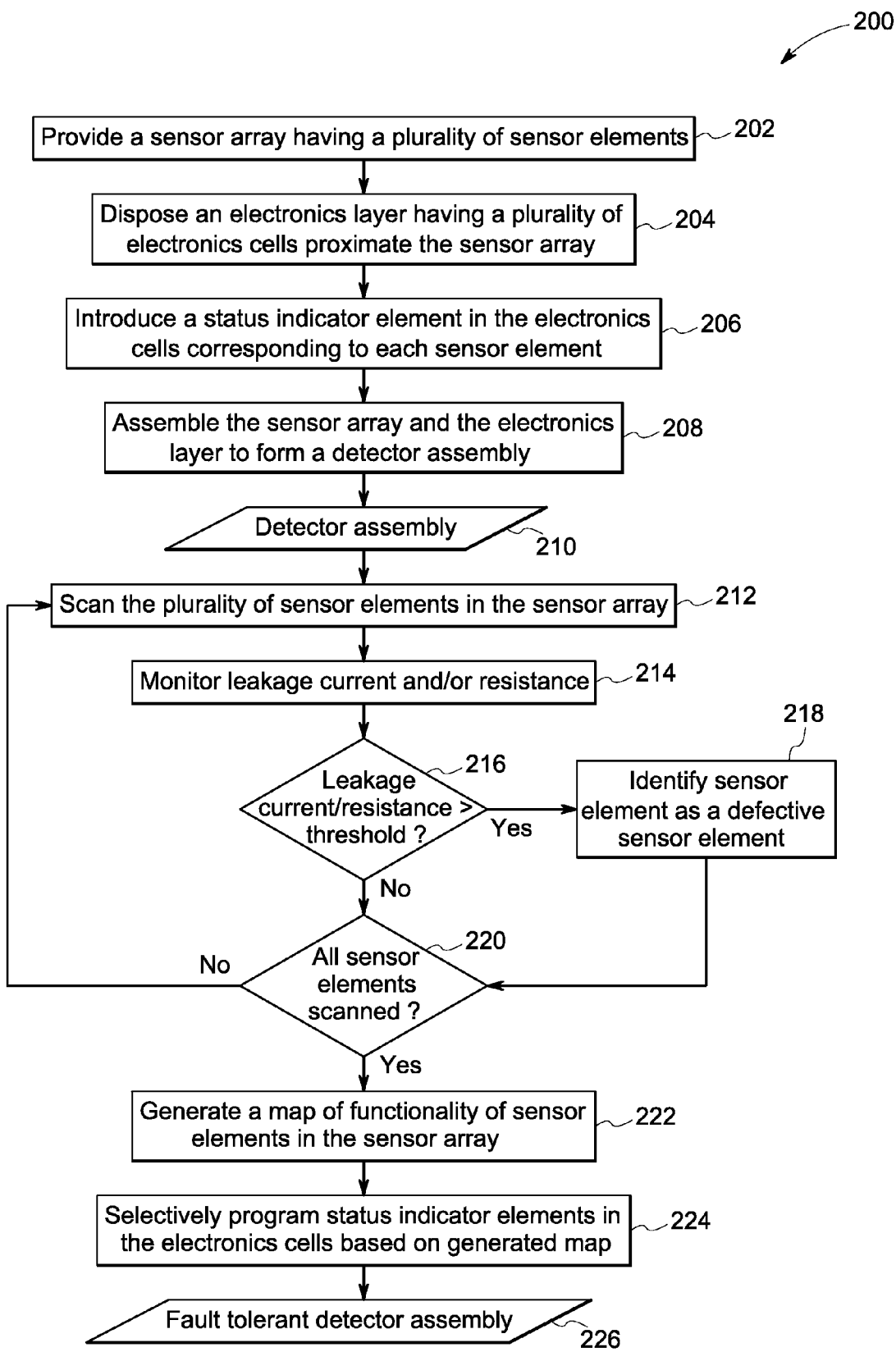
FIG. 2 is a diagrammatic illustration of a method for forming an exemplary fault tolerant detector assembly for use in the system of FIG. 1, in accordance with aspects of the present disclosure.

FIG. 2 is a flow chart 200 illustrating exemplary logic of a method of forming a fault tolerant detector assembly for use in a system, such as, but not limited to the ultrasound imaging system 100 of FIG. 1. The detector assembly so formed may be used to sense a plurality of input signals. As used herein, the term "detector assembly" is used to refer to a determined arrangement that includes at least one sensor array and at least one layer of electronics corresponding to the sensor array. Also, the term "sensor array" is used to refer to an arrangement of one or more sensors or sensor elements. In addition, the term "electronics layer" is used to refer an arrangement of one or more electronics cells that correspond to the one or more sensor elements in the sensor array and other electronics.

Furthermore, it may be noted that in one embodiment, the term "large area planar detector" is used to refer to a detector that is formed by arranging a plurality of assemblies such that the plane of the detector assemblies is locally normal to the detector normal and the detector has a locally smooth surface. It may further be noted that the planar detector may include a flat panel detector or an arc detector.

As illustrated in FIG. 2, the method starts at step 202, where a sensor array may be provided. As previously noted, the sensor array may include a plurality of sensor elements arranged in a determined pattern, where the sensor elements are configured to detect input signals, such as radiation signals, acoustic signals, light signals, and the like. Each of the one or more sensor elements has a respective first side and a second side. In certain embodiments, the first side of the one or more sensor elements is configured to receive the input signals. Also, a plurality of contact pads may be disposed on the second side of each sensor element. It may be noted that in some embodiments, each sensor element may have only one contact pad disposed on the second side. These contact pads are employed to operationally couple the sensor elements in the sensor array to the integrated circuit.

Subsequently, as depicted by step 204, an electronics layer may be provided. In particular, the electronics layer may be disposed in close proximity to the sensor array. As previously noted, the electronics layer may include one or more electronics cells corresponding to the sensor elements in the sensor array. In one embodiment, the electronics layer may include one or more integrated circuits. Moreover, in one embodiment, the one or more integrated circuits may be coupled to a substrate using conventional assembly methods such as wire bonding or flip chip attach. It may be noted that in certain embodiments, the one or more integrated circuits may include an application specific integrated circuit (ASIC). Furthermore, a plurality of contact pads may be disposed on a first side of each of the one or more integrated circuits. These contact pads aid in coupling the integrated circuits to the corresponding one or more sensor elements in the sensor array. Additionally, these contact pads also facilitate power and/or digital communication connections from the integrated circuits to other system electronics, such as the system electronics in the substrate.

It may be noted that the substrate has a first side and a second side. Also, the substrate may be a rigid substrate or a flexible substrate. In one embodiment, the rigid substrate may be formed using high-density organic materials such as a multi-layered substrate made of expanded Teflon, such as Rogers 2800, FR4 or BT laminate materials. Alternatively, an inorganic material such as ceramic (96% Alumina) or a Si interposer may be employed to form the rigid substrate. Furthermore, the flexible substrate may be formed using polyimide thin films. Moreover, the substrate may be representative of a backplane layer that includes other system electronics, in certain embodiments.

Furthermore, as previously noted, the sensor array is disposed in close proximity to the electronics layer. Defects in the sensor elements can potentially affect the operation of the respective electronics cells and or the entire system that includes the sensor array. Also, defects in the sensor elements may affect the yield of the sensor array. Accordingly, it is desirable to identify poorly yielding sensor elements in the sensor array and exclude these poorly yielding sensor elements from operation.

In accordance with exemplary aspects of the present disclosure, a method for identifying and excluding the poorly yielding sensor elements from operation, is presented. Particularly, once the poorly yielding sensor elements are identified, the electronics cells corresponding to these sensor elements may be selectively programmed to be insensitive to the poorly yielding sensor elements or to otherwise enhance the performance of the sensor elements. In addition, the method allows for defects in the sensor elements to be located and mitigated even after sensor array is operatively coupled to the electronics layer. It may be noted that the terms defective sensor elements and poorly yielding sensor elements may be used interchangeably.

Moreover, as noted hereinabove, the poorly yielding sensor elements may be identified and the electronics corresponding to these sensor elements may be programmed to be insensitive to the poorly yielding sensor elements. To that end, in accordance with aspects of the present disclosure, a status indicator element may be provided in the electronics cells corresponding to each sensor element, as indicated by step 206. In one embodiment, the status indicator element may include one or more memory elements. By way of example, the status indicator element may include a random access memory (RAM), dynamic random access memory (DRAM), static random access memory (SRAM), read only memory (ROM), electrically erasable programmable read only memory (EEPROM), programmable fuses and laser trim resistors, floating gate trimming technology or capacitors for storing analog voltages for adjustment of respective bias voltages, and the like.

The status indicator element in the electronics cell may be employed to store a "status" of a corresponding sensor element. In one example, the status of the sensor element may be indicative of a defective/poorly yielding sensor element or a functional sensor element. By way of example, a status of "1" or a "high" in the status indicator element may be indicative of a defective/non-functioning sensor element, while a status of "0" or a "low" in the status indicator element may be indicative of an operational sensor element. In certain embodiments, an initial state of the status indicator elements may be set to a "0" value. It may be noted that a first value or a first status value may be indicative of an operational status of a sensor element, while a second value or a second status value may be indicative of a defective of poorly yielding status of a sensor element.

Subsequently, at step 208, the sensor array may be operatively coupled to the electronics cells in electronics layer having the exemplary status indicator elements to form an exemplary detector assembly 210. In one embodiment, vias may be employed to operatively couple the one or more sensor elements to the corresponding electronics cells. In some embodiments, the sensor elements may be coupled to the electronics cells using either flip chip attach (FCA) or wire bonding of the ASIC die. Moreover, in certain embodiments, the sensor elements may be coupled to the electronics cells using a FCA process or a gold-stud bump on the die surface along with silver-fill conductive epoxy. Also, in yet another embodiment, any intervening devices disposed between a sensor element and the corresponding integrated circuit/electronics cell may be employed to operatively couple the sensor elements to the corresponding electronics cells. Furthermore, in certain embodiments, the sensors may be built directly above the electronics cells by pre-processing and/or post-processing of the electronics wafers.

Once the exemplary detector assembly 210 is formed, in accordance with aspects of the present disclosure, the sensor array in the detector assembly 210 may be scanned to identify any defective or poorly yielding sensor elements, as indicated by step 212. In one example, if the sensor array includes a two-dimensional (2D) array having m rows and n columns, each sensor element in each row may be scanned in a serial fashion to determine the "status" of the sensor elements. In one example, the sensor array may be scanned at a manufacturing facility for example, during the fabrication of the detector assembly 210 to locate any defective sensor elements. However, the sensor array may also be periodically scanned during operation to identify any defective sensor elements. Additionally, in accordance with further aspects of the present disclosure, the plurality of sensor elements in the sensor array may also be scanned by monitoring behavior of the sensor elements in response to variations in frequency and/or bias voltage.

It may be noted that an increase in current drawn by the sensor array may be indicative of a fault/defect in one or more sensor elements in the sensor array. For example, if the sensor array includes a Capacitive Micromachined Ultrasound Transducers (cMUT) array, a short between a signal terminal and a bias terminal corresponding to a sensor element may force the global high voltage bias terminal to the signal terminal voltage (nominally 0 V) and create an increase in leakage current due to that sensor element. The amount of leakage on each sensor element and the number of sensor elements affected may result in excessive loading of the bias voltage generator circuit and consequent loss in global bias level, which in turn may lead to diminished performance of the entire sensor array.

In accordance with aspects of the present disclosure, the current, such as a leakage current in the sensor array, may be monitored to aid in detecting any defective sensor elements in the sensor array, as depicted by step 214. It may be noted that at step 214 an aggregate resistance of the sensor array may also be employed to aid in identifying any defective sensor elements. The current corresponding to each sensor element may be compared with a threshold current value. Accordingly, at step 216, a check may be carried out to verify if a present value of the current in a sensor element is greater than the threshold current value. If it is determined that the present value of current is greater than the threshold current value, then that sensor element may be identified as a defective sensor element, as indicated by step 218. In one example, a defective sensor element may be representative of a shorted sensor element. These shorted sensor elements, for example, may diminish the performance of the system employing the sensor array. Control may then be passed on to step 220.

With returning reference to step 216, if the present value of the leakage current is less than the threshold current value, another check may be carried out to verify if all the sensor elements in the sensor array have been scanned, as depicted by step 220. At step 220, if it is determined that all the sensor elements have not been scanned, control may be returned to step 212 and steps 212-220 may be repeated. However, at step 220, if it is determined that all the sensor elements in sensor array have been scanned, then control may be passed to step 222.

In accordance with further aspects of the present disclosure, once all the sensor elements have been scanned and defective sensor elements, if any, have been identified, a functionality map that is representative of the functioning of the sensor elements in the sensor array may be generated, as indicated by step 222. In one embodiment, the map may be generated during manufacturing of the detector assembly. In another embodiment, the map may be periodically generated during operation of the sensor array in the detector assembly.

Furthermore, the map so generated may include information regarding the status of all the sensor elements in the sensor array. In one example, the information may include data such as, but not limited to, shorting between sensor element signal terminals and bias terminals, shorting between neighboring sensor elements, reduced sensor element sensitivity, increased leakage current, and the like.

In accordance with aspects of the present disclosure, the map generated at step 222 may be employed to program control information into the electronics layer, thereby allowing the individual electronics cells in the electronics layer to mitigate the poor yield of corresponding defective sensor elements. In particular, effects of these defective sensor elements may be mitigated by locating the defective sensor elements and programming a corresponding status indicator element. By way of example, once a defective sensor element is identified, a state of the status indicator element in the electronic cell corresponding to the identified defector sensor element may be selectively programmed to take into account defects in that sensor element, as depicted by step 224.

To that end, in one embodiment, an address of the electronics cell corresponding to the defective sensor element may be determined. Furthermore, the state of the status indicator element corresponding to the defective sensor element may be set to indicate the defective state of the sensor element. As noted hereinabove, the status indicator element is employed to store the "status" of a corresponding sensor element. Accordingly, in one example, a status of "1" or a "high" may be written in the status indicator element corresponding to the defective sensor element to indicate a defective/non-functioning sensor element. It may be noted that a state of "0" or a "low" in the status indicator element may be indicative of a functioning/operational sensor element. In one example, a digital bus may be employed to selectively program the status indicator elements.

Additionally, a "1" state of the status indicator elements corresponding to the defective sensor elements may be configured to force the respective sensor elements to permanently turn off or disable corresponding transmit/receive switches. Moreover, the "1" state of the status indicator elements may also be configured to drive corresponding output signals to a voltage that is substantially similar to the bias voltage. In certain other embodiments, the identified defective sensor elements may be excluded from operation by deactivating the transmitter of the defective sensor elements, deactivating the transmit/receive switch of the defective sensor elements, or a combination thereof. Accordingly, the state of the electronics cells in the electronics layer may be changed to compensate for the defective sensor elements. Consequently, the operation of the entire sensor array may not be affected since the bias voltage is no longer pulled down to ground.

According to further aspects of the present disclosure, local control voltages may be programmed to mitigate the effect of spatially distributed bias voltages in the sensor array. In addition, static current values may be programmed to counter the effects of spatially distributed leakage currents. For example, impedance of the sensor array as a function of frequency may be measured. Additionally, a corresponding bias voltage trimming value for every sensor element in the sensor array may be determined in order to obtain a more regular response distribution across the sensor array. In this case, an N-bit word corresponding to a local bias voltage adjustment for each sensor element may be written to the respective status indicator elements of each electronics cell. Also, the N-bit word may include a 3-bit word, in one example. The N-bit status word may be configured to drive a local digital to analog converter (DAC) to generate a bias voltage adjustment for the sensor element corresponding to that electronics cell. This bias voltage adjustment may be applied to change the ground value locally away from the nominal 0 V value on transmit and receive to effect the change in the overall bias voltage seen by the respective sensor element. This adjustment may mitigate the effects of pull-in voltage variation, which in turn reduces the overall sensitivity of the sensor array since some sensor elements may collapse early in response to the bias voltage being ramped up from 0 V, while other sensor elements may collapse at a higher voltage Implementing the sensor array as described hereinabove allows a more uniform sensor array that can be biased much closer to collapse overall, thereby ensuring optimum sensitivity for imaging. Furthermore, analog trim voltages may also be stored locally using floating gate trimming technology, analog capacitors, trimmable resistors, and the like.

In accordance with further aspects of the present disclosure, the step of comparing one or more of the current and the resistance to the threshold value may be performed globally for the entire sensor array to determine if the sensor array has existing defective or poorly yielding sensor elements. Once the poorly yielding sensor elements are identified at the global level of the sensor array, the individual sensor elements may then be scanned to identify other poorly yielding defective ones, if needed.

It may be noted that a leakage current in the sensor array may be dependent upon a number of poorly yielding or defective sensor elements in that sensor array. In particular, an increase in the number of poorly yielding sensor elements may result in an increase in the leakage current in the sensor array. Accordingly, a leakage current in the entire sensor array may be monitored. This monitored leakage current may be used to estimate the number of poorly yielding sensor elements. By way of example, if the sensor array draws a current of about 100 µA, then it may be estimated that the sensor array includes one poorly yielding element. Accordingly, if the measured/monitored leakage current corresponding to the sensor array is about 1 mA, then it may be estimated that the sensor array includes about 10 poorly yielding sensor elements.

Furthermore, if the number of poorly yielding sensor elements is greater than a desired threshold value, it may be desirable to identify those sensor elements and disable the poorly yielding sensor elements during operation of the sensor array. To that end, in accordance with aspects of the present disclosure, the leakage current may be compared with a threshold leakage current value. If the measured leakage current is greater than the threshold leakage current value, it may be determined that the estimated number of poorly yielding sensor elements is greater than the desired threshold value. Accordingly, in this case, it may be desirable to scan the sensor elements in the sensor array to identify and disable the poorly yielding sensor elements. By way of example, a measured leakage current of about 1 mA may be less than the threshold leakage current value and may be indicative of about 10 poorly yielding sensor elements in the sensor array, as noted hereinabove. However, a measured leakage current of about 20 mA may be greater than the threshold leakage current value and generally indicative of excessive leakage current in the sensor array. Based on the measured leakage current value, it may be estimated that the sensor array includes about 200 poorly yielding elements. In this case it may be desirable to scan the entire sensor array to identify and disable the 200 poorly yielding sensor elements.

Consequent to the processing of steps 202-224, a fault tolerant detector assembly 226 may be formed. It may be noted that the status indicator elements may be programmed based on the map generated at step 222 either during manufacture or periodically during operation.

Figure 3:
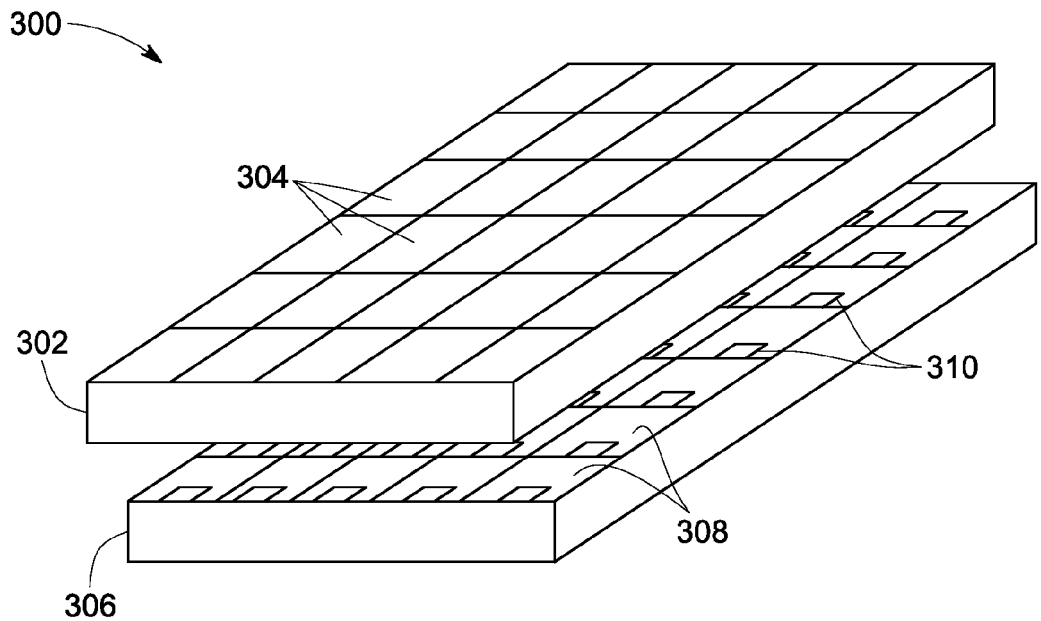
FIG. 3 is a diagrammatic illustration of an embodiment of an exemplary detector assembly, in accordance with aspects of the present disclosure.

Referring now to FIG. 3, a diagrammatical representation 300 of an exemplary embodiment of a fault tolerant detector assembly, in accordance with aspects of the present disclosure, is depicted. The fault tolerant detector assembly 300 may include a sensor array 302. The sensor array 302 may include a plurality of sensor elements 304 disposed in a determined pattern. In one example, the sensor array 302 may include the plurality of sensor elements 304 arranged in a 2D array having m rows and n columns.

In addition, the fault tolerant detector assembly 300 may also include an electronics layer 306. The electronics layer 306 may include electronics cells 308 corresponding to each sensor element 304. In accordance with exemplary aspects of the present disclosure, the electronics cells 308 corresponding to each sensor element 304 may include a status indicator element 310 that is configured to store a current state of the corresponding sensor element 304.

As previously described with reference to FIG. 2, the sensor array may be scanned to determine a current status of each sensor element. Furthermore, in one embodiment, the leakage current or resistance corresponding to that sensor element may be monitored. The measured leakage current may be compared with a threshold value of leakage current. If it is determined that the value of the leakage current is greater than the threshold value, then that sensor element may be identified as a defective sensor element or a poorly yielding sensor element. Accordingly, the status indicator element 310 corresponding to that sensor element 304 may be set to a "1" or a "high." However, if it is determined that the leakage current corresponding to the sensor element is lower than the threshold leakage current value, then that sensor element may be identified as a functioning sensor element. The status indicator element corresponding to this sensor element may be maintained at or set to a "0" or a "low" value Implementing the detector assembly as described hereinabove results in a "fault tolerant" detector assembly 300 as the state of the electronics cells 308 in the electronics layer 306 may be changed to compensate for the defective sensor elements in the sensor array 302, thereby increasing the yield of the sensor array and/or enhancing the performance of the detector assembly 300.

Figure 4:
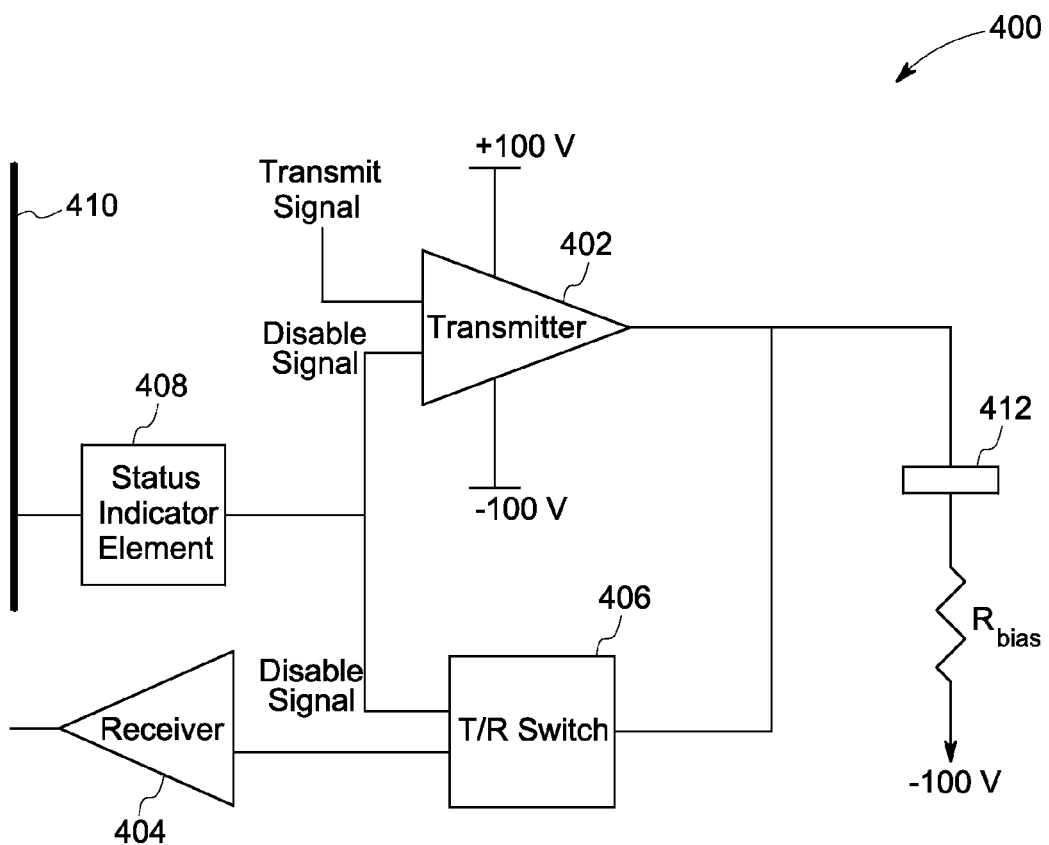
FIG. 4 is a diagrammatic illustration of a unit element cell of the detector assembly of FIG. 3 that includes a sensor element along with an electronics cell having a corresponding status indicator element, in accordance with aspects of the present disclosure.

Turning now to FIG. 4, a diagrammatical representation 400 of an exemplary unit element cell is depicted. The term unit element cell as used herein is used to refer to a sensor element, such as the sensor element 304 (see FIG. 3) along with a corresponding electronics cell such as the electronics cell 308 (see FIG. 3) having a corresponding status indicator element, such as the status indicator element 310 (see FIG. 3). Moreover, the electronics cell may also include a transmitter or a pulser 402, a receiver 404, a transmit/receive switch 406, and a status indicator element 408.

Reference numeral 410 is generally representative of a digital bus. The digital bus 410 may be employed to set the status of the status indicator element 408. By way of example, in a sensor array that is composed of such cells 400, a "1" state of the status indicator elements corresponding to the defective sensor elements may be configured to force respective sensor elements 412 to deactivate corresponding transmitters 402 and/or transmit/receive switches 406. In addition, as previously noted, the "1" state of the status indicator elements may also be configured to drive corresponding output signals at a signal terminal to be substantially equal to a voltage at a bias terminal. It may be noted that driving the voltage at the sensor element to be substantially equal to the voltage at the bias terminal results in a 0 V bias across the sensor element. Consequently, that sensor element may be shorted out or disabled from operation, thereby preventing the sensor element from leaking and drawing down the global supply voltage. In one embodiment, the voltage at the signal terminal may be equal to the voltage at the bias terminal. However, in certain other embodiments, the voltage at the signal terminal may differ from the voltage at the bias terminal in a range from about +/−5% to about +/−10% of the bias terminal voltage. The state of the electronics cells in the electronics layer may thus be changed to compensate for the defective sensor elements.

Figure 5:
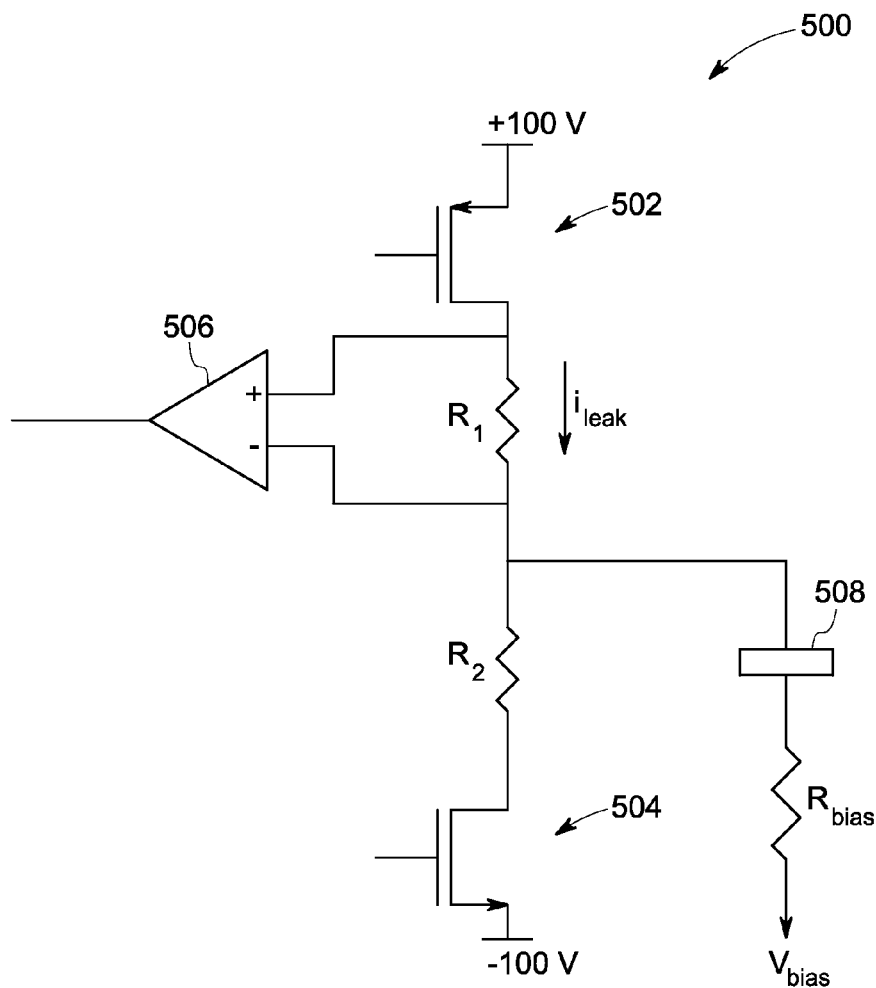
FIG. 5 is a diagrammatic illustration of a cell in a transmitter of the sensor element of FIG. 4, in accordance with aspects of the present disclosure.

FIG. 5 is a diagrammatical representation 500 of an exemplary implementation of a cell. In particular, the cell 500 is a diagrammatical representation of a transmitter such as the transmitter 402 of FIG. 4. In a sensor array which includes sensor elements that are composed of such cells 500, each cell 500 may be configured to independently monitor a leakage current in that cell. In one embodiment, the cell 500 may include a pMOSFET device 502 operatively coupled to an nMOSFET device 504 via one or more resistances such as $R_1$ and $R_2$.

In accordance with aspects of the present disclosure, the cell 500 may be configured to monitor an output via use of an operational amplifier 506, for example. By way of example, a current flowing from a transmitter output device, such as the pMOSFET device 502 may be measured as a voltage across a resistor such as the resistor $R_1$ between the drive transistor and a sensor element 508. Although the embodiment of FIG. 5 is shown as including an operational amplifier across the resistor $R_1$, use of an operational amplifier across the resistor $R_2$ or both $R_1$ and $R_2$ is also envisaged.

Moreover, in accordance with aspects of the present disclosure, when the measured voltage rises above a determined threshold value, a status indicator element corresponding to that cell may be set to '1' indicating that the cell is defective and needs to be excluded during operation of the sensor array. In particular, when the measured voltage is greater than the determined threshold value, the transmitter and/or the transmit/receive switch corresponding to that cell may be disabled. It may be noted that in one embodiment, logic such as a comparator may be used to compare the measured voltage with the determined threshold value. Also, information regarding the status of the status indicator elements may be read out to a control system in order to generate a map that is representative of the defective elements in the sensor array. Implementing a sensor array having the sensor elements as described hereinabove aids in forming a self-monitoring sensor array, thereby circumventing the need for external circuitry to monitor the sensor array.

Figure 6:
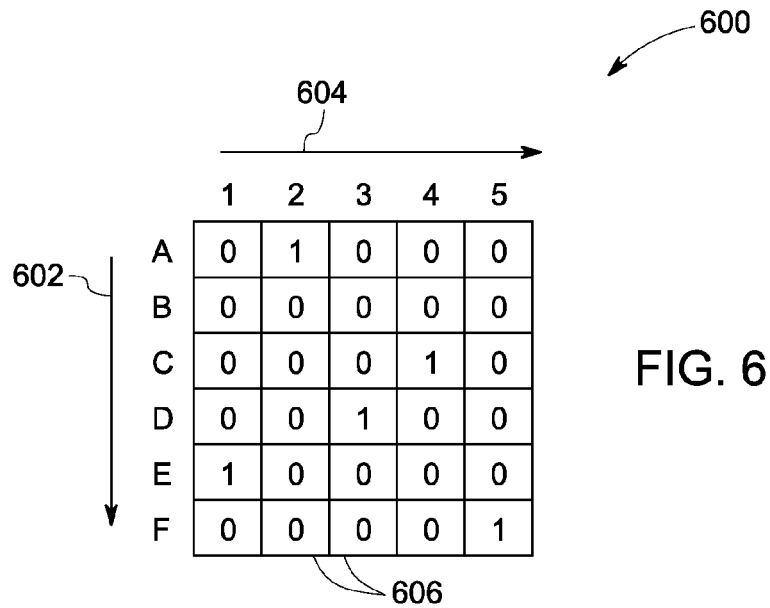
FIG. 6 is a diagrammatic illustration of a functional map, in accordance with aspects of the present disclosure.

FIG. 6 is a diagrammatical representation 600 of an example of a functionality map corresponding to a sensor array, such as the sensor array 302 of FIG. 3. In the example of FIG. 3, the sensor array is depicted as including a plurality of sensor elements 304 arranged in 6 rows and 5 columns. Accordingly, the functionality map 400 may also include a plurality of cells 606 arranged in a pattern of 6 rows and 5 columns, in one example. Rows 602 in the map 600 may be represented as "A", "B", "C", "D", "E", and "F," while columns 604 may be represented as "1", "2", "3", "4", and "5." In addition, the status indicator element corresponding to the each sensor element may be set to a "1" or a "0" based on a current state of the sensor element. By way of example, an initial state of the status indicator elements may be "0." Consequent to the scanning process (see step 212 of FIG. 2), one or more defective sensor elements may be identified and corresponding addresses may be determined. Also, the status indicator elements corresponding to the defective sensor elements may be selectively programmed to a "1." In the example of FIG. 4, cells A2, C4, D3, E1 and F5 in the map 600 may be set to a value of "1" to indicate the defective status of the corresponding sensor elements.

In one example, this map 600 may be generated during manufacturing of an exemplary detector assembly, such as the detector assembly 300 of FIG. 3. In this example, the status indicator elements may be programmed based on the map 600 during the fabrication process to identify the defective sensor elements. Alternatively, the map 600 may also be generated during periodic monitoring of the detector assembly during operation. To that end, the detector assembly may be periodically scanned while in operation to identify the poorly yielding or defective sensor elements and a map representative of the defective sensor elements may be generated. In this example, once the detector assembly is formed, the status indicator elements corresponding to the identified poorly yielding or defective sensor elements may be set to a "1" for example.

Moreover, in accordance with further aspects of the present disclosure, the global leakage current of the sensor array may be monitored continuously during use as a general indicator of the health of the sensor array. If an increase in global leakage current is detected at any time, the sensor array may be deactivated and scanned for poorly yielding sensor elements. The identified poorly yielding sensor elements may then be disabled.

Implementing the fault tolerant detector assembly as described hereinabove aids in protecting the electronics from shorts to the high voltage bias terminal through the sensor elements which may occur at any time during the operation of the detector assembly. In addition, the measured leakage current values may also be recorded. Trends of the measured leakage current values may be followed over time as a means to predict future potential failures of the sensor array.

It may be noted, if there exists a previously determined map corresponding to the sensor array, that map may be updated based on the periodical scan of the sensor array. Furthermore, once an imaging system including the exemplary detector assembly, such as the imaging system 100 of FIG. 1 is energized, the map corresponding to that sensor array may be retrieved from a data repository, such as the data repository 134 (see FIG. 1), for example. The map may be used to identify locations of any defective sensor elements. Accordingly, any data from the defective sensor elements may be discounted during a data acquisition process.

It may be noted that in certain situations, it may be desirable to employ large area detectors to aid in imaging a large object such as luggage, a package, or relatively large anatomical regions of interest in the patient 101 (see FIG. 1). To that end, in accordance with further aspects of the present disclosure, the exemplary detector assembly, such as the fault tolerant detector assembly 300 (see FIG. 3) may be arranged in determined pattern on a support structure to form a large area detector.

As described hereinabove, it may be desirable to form a substantially planar detector assembly in which the sensor elements are assembled on one side of the substrate, for example, and the one or more integrated circuits (IC) are assembled on the other side of the substrate to form a tileable module or unit. An array of these modules or units may then be assembled to the next level of carrier to produce a larger detector.

Figure 7:
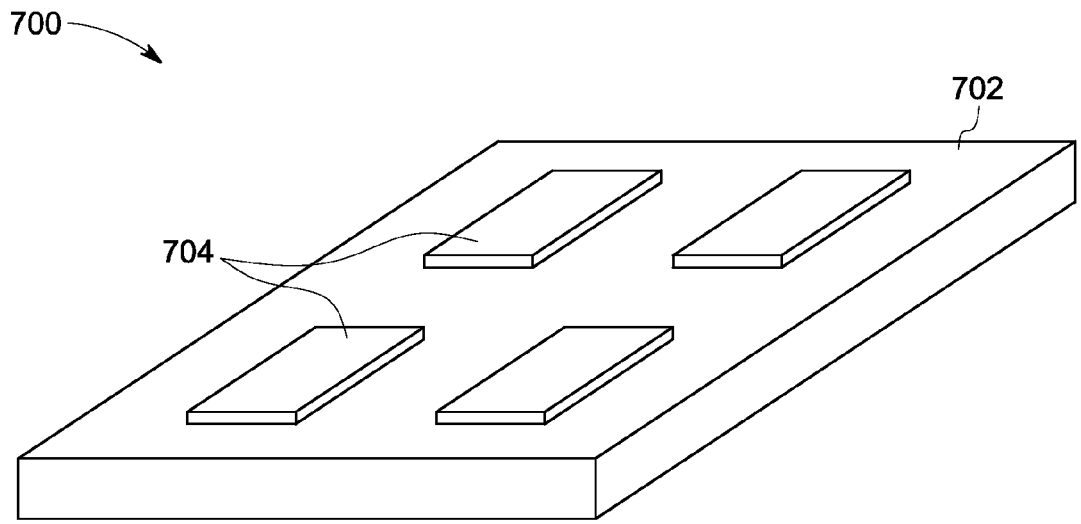
FIG. 7 is a diagrammatic illustration of an exemplary large area detector formed using the detector assemblies of FIG. 3, in accordance with aspects of the present disclosure.

FIG. 7 depicts one embodiment 700 of a substantially planar large area detector array. Particularly, a plurality of detector assemblies 704 such as the detector assembly 300 (see FIG. 3) may be tiled on a first side of a support structure 702. The support structure 702 may be a flexible substrate or a rigid substrate. Also, the substrate 702 may be formed employing circuit boards materials such as FR4, BT-Epoxy, CEM-1,5, Teflon, polytetrafluoroethylene (PTFE), glass, ceramic, or polyimide. The plurality of detector assemblies 704 may be arranged on the support structure 702 in a determined pattern based on an application to form the substantially planar detector array 700.

Specifically, the plurality of fault tolerant detector assemblies 704 may be tiled on the first side of the support structure 702 to form a substantially planar large area fault tolerant detector 700. In one embodiment, wire bonds and/or other interconnect may be used to operationally couple the detector assemblies 704 to the other system electronics. The use of the detector assemblies 704 allows the detector assemblies 704 to be tiled on the support structure 702 to form the substantially planar large area detector 700 that is constructed with detector assemblies 704 that are all disposed in the same plane. In addition, these detector assemblies 704 allow creation of detector arrays of different geometries while maintaining a small pitch sensor.

Image data acquired from the fault tolerant detector assembly may be used to reconstruct images of an object of interest such as anatomical region of interest in the patient 101 or a package, baggage, and the like. Once reconstructed, the image produced by the system 100 of FIG. 1 that employs the exemplary fault tolerant detector assembly reveals internal features of the patient 101, for example. In traditional approaches for the diagnosis of disease states, and more generally of medical conditions or events, a radiologist or physician typically considers the reconstructed image to discern characteristic features of interest. In cardiac imaging, such features include coronary arteries or stenotic lesions of interest, and other features, which would be discernible in the image, based upon the skill and knowledge of the individual practitioner. Other analyses may be based upon capabilities of various algorithms, including algorithms generally referred to as computer-aided detection or computer-aided diagnosis (CAD) algorithms.

Figure 8:
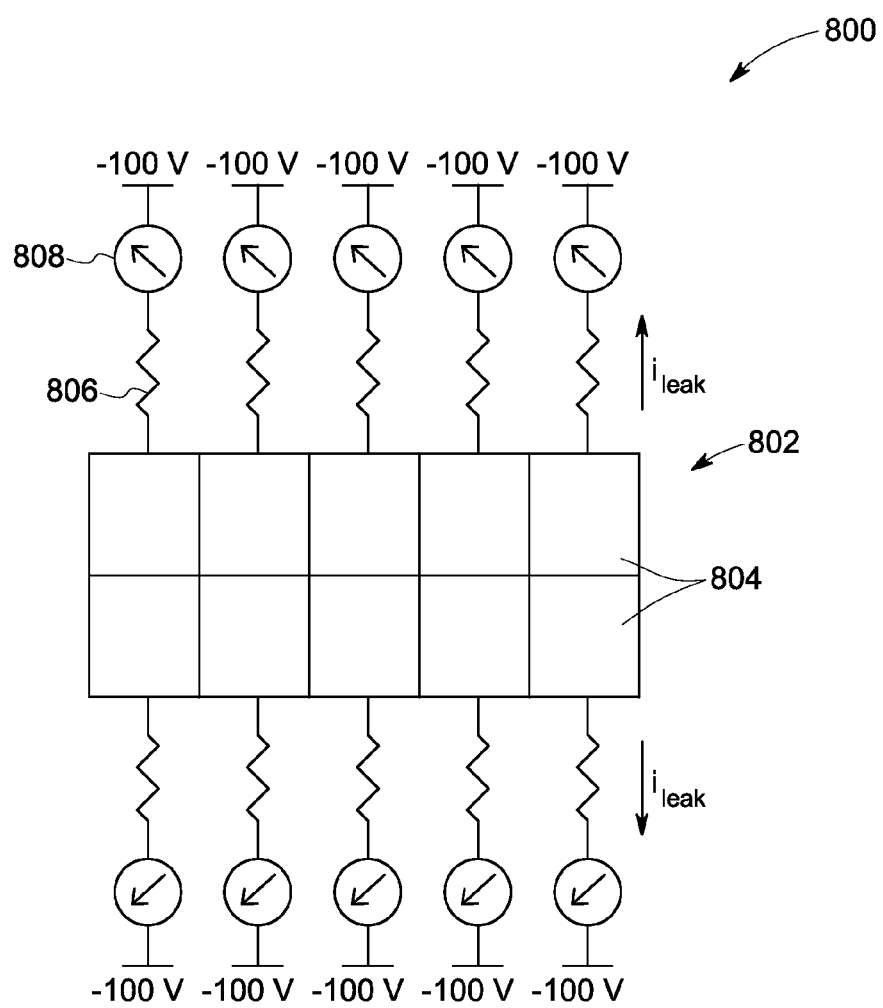
FIG. 8 is a diagrammatic illustration of another exemplary large area detector formed using the detector assemblies of FIG. 3, in accordance with aspects of the present disclosure.

FIG. 8 depicts an exemplary configuration 800 of a large area sensor array 802. In accordance with aspects of the present disclosure, the large area sensor array 802 may organized such that the time taken to scan the entire array is substantially reduced. Specifically, the sensor array 802 may divided up into a plurality of smaller sub-arrays 804. Moreover, global leakage current corresponding to each of these sub-arrays 804 may be measured independently. It may be noted that these sub-arrays 804 may be simultaneously scanned in parallel to identify defective sensor elements in the plurality of sub-arrays 804. Consequently, the time taken to scan the sensor array 802 is substantially reduced. By way of example, the time taken to scan the sensor array 802 may be reduced by a factor equal to the number of sub-arrays 804 in the sensor array 802. Reference numeral 806 is generally representative of a resistor. Moreover, a current measuring device 806 may be used to monitor a current in a corresponding sub-array 802. In one embodiment, the current measuring device 808 may include an ammeter. In accordance with aspects of the present disclosure, scanning may also be controlled by a field programmable gated array (FPGA), an ASIC, or an embedded microprocessor that may be disposed adjacent the sensor array in probe handle. Moreover, the scanning may also be controlled by very large scale integrated (VLSI) logic implemented directly on the same ASIC as the electronics cells.

Furthermore, the foregoing examples, demonstrations, and process steps such as those that may be performed by the imaging system 100 may be implemented by suitable code on a processor-based system, such as a general-purpose or special-purpose computer. It should also be noted that different implementations of the present disclosure may perform some or all of the steps described herein in different orders or substantially concurrently, that is, in parallel. Furthermore, the functions may be implemented in a variety of programming languages, including but not limited to C++ or Java. Such code may be stored or adapted for storage on one or more tangible, machine readable media, such as on data repository chips, local or remote hard disks, optical disks (that is, CDs or DVDs), memory or other media, which may be accessed by a processor-based system to execute the stored code. Note that the tangible media may comprise paper or another suitable medium upon which the instructions are printed. For instance, the instructions may be electronically captured via optical scanning of the paper or other medium, then compiled, interpreted or otherwise processed in a suitable manner if necessary, and then stored in the data repository 132 or memory.

The methods for forming the fault tolerant detector assembly and the various embodiments of the fault tolerant detector assembly described hereinabove dramatically increase the yield of the sensor arrays. The increased yield also facilitates forming large area detectors. Additionally, use of the fault tolerant detector assembly enhances the performance of the imaging system that employs the detector assembly. In particular, the system and method provide the ability to locate poorly yielding sensor elements within the sensor array and exclude these poorly yielding sensor elements from operation by programming corresponding electronics to be insensitive to these sensor elements. Moreover, the fault tolerant detector assembly allows for defects in the sensor array to be located and mitigated even after the sensor array has already been assembled into the detector assembly.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method for forming a fault tolerant detector assembly, comprising:
providing a sensor array having a plurality of sensor elements;
providing an electronics layer having a plurality of electronics cells, wherein the plurality of electronics cells corresponds to the plurality of sensor elements in the sensor array;
introducing a status indicator element in each of the plurality of the electronics cells, wherein the status indicator element is configured to store a status of a corresponding sensor element, and wherein a first value of the status comprises an operational status of the corresponding sensor element and a second value of the status comprises a poorly yielding status of the corresponding sensor element;
scanning the plurality of sensor elements in the sensor array to identify the status of the plurality of sensor elements in the sensor array;
generating a functionality map based on the identified status of the plurality of sensor elements in the sensor array;
selectively programming the status indicator elements based on the functionality map to form a fault tolerant detector assembly, wherein selectively programming the indicator elements based on the functionality map comprises changing a status of a status indicator element from a first value to a second value based on the functionality map; and
excluding, during operation of the fault tolerant detector assembly, sensor elements corresponding to electronics cells having an associated status indicator element set to the second value, wherein excluding the sensor elements comprises configuring the sensor elements to drive a signal terminal such that a signal terminal voltage is equal to a bias terminal voltage of the corresponding sensor element.

2. The method of claim 1, wherein the sensor array comprises a computed tomography detector array, an X-ray detector array, a photon-counting X-ray detector, an ultrasound transducer array, or combinations thereof.

3. The method of claim 1, further comprising operatively coupling the sensor array to the electronics layer.

4. The method of claim 1, wherein the status indicator element comprises one or more memory elements.

5. The method of claim 1, further comprising setting the status of the status indicator element in each of the plurality of the electronics cells to the first value, wherein the first value is representative of the operational status of a corresponding sensor element.

6. The method of claim 1, wherein the status of the plurality of sensor elements is based on a distribution of states corresponding to one or more bits in the status indicator element, and wherein the one or more bits represent an analog value.

7. The method of claim 6, further comprising setting the status of the status indicator element in each of the plurality of electronics cells by adjusting a sensor bias voltage of a corresponding sensor element.

8. The method of claim 1, wherein scanning the plurality of sensor elements in the sensor array comprises monitoring one or more of a current and a resistance corresponding to the plurality of sensor elements.

9. The method of claim 8, further comprising comparing one or more of the current and the resistance to a threshold value.

10. The method of claim 9, further comprising categorizing a sensor element as a poorly yielding sensor element if one or more of the current and the resistance is greater than the threshold value.

11. The method of claim 1, wherein excluding the sensor elements comprises deactivating a transmitter of the excluded sensor elements, deactivating a transmit/receive switch of the excluded sensor elements, or a combination thereof.

12. The method of claim 1, wherein excluding the sensor elements comprises:
measuring one or more of the current and the resistance in each sensor element; and automatically disabling a sensor element based on the measured value of the current or the resistance.

13. The method of claim 1, wherein scanning the plurality of sensor elements in the sensor array comprises monitoring a behavior of the plurality of sensor elements with respect to frequency and a bias voltage.

14. The method of claim 1, wherein scanning the plurality of sensor elements in the sensor array comprises:
independently measuring a current in each sensor element; and
automatically disabling the sensor element based on a value of the measured current in the sensor element.

15. A fault tolerant detector assembly, comprising:
a sensor array having a plurality of sensor elements; and
an electronics layer having a plurality of electronics cells corresponding to the plurality of sensor elements, wherein each of the plurality of electronics cells comprises a status indicator element configured to store a status of a corresponding sensor element, wherein the status indicator elements corresponding to the plurality of electronics cells are selectively programmed based on a functionality map to change a status of a status indicator element from a first value to a second value based on the functionality map, wherein during operation of the fault tolerant detector assembly, sensor elements corresponding to electronics cells having an associated status indicator element set to the first value are included and sensor elements corresponding to electronics cells having an associated status indicator element set to the second value are excluded, and wherein the sensor elements are excluded by configuring the sensor elements to drive a signal terminal such that a signal terminal voltage is equal to a bias terminal voltage of the corresponding sensor element.

16. The fault tolerant detector assembly of claim 15, wherein the plurality of sensor elements in the sensor array is scanned to identify the status of the plurality of sensor elements in the sensor array.

17. The fault tolerant detector assembly of claim 15, wherein the functionality map comprises the status of each of the plurality of sensor elements.

18. The fault tolerant detector assembly of claim 15, wherein the first value of a sensor element comprises an operational status, and wherein the second value of a sensor element comprises a poorly yielding status.

19. The fault tolerant detector assembly of claim 15, wherein the sensor array comprises a computed tomography detector array, an X-ray detector array, an ultrasound transducer array, or combinations thereof.

20. The fault tolerant detector assembly of claim 15, wherein the status indicator element comprises at least one memory element.

21. A method for forming a fault tolerant detector assembly, comprising:
providing a sensor array having a plurality of sensor elements;
providing an electronics layer having a plurality of electronics cells, wherein the plurality of electronics cells corresponds to the plurality of sensor elements in the sensor array;
introducing a status indicator element in each of the plurality of the electronics cells, wherein the status indicator element is configured to store a status of a corresponding sensor element, and wherein a first value of the status comprises an operational status of the corresponding sensor element and a second value of the status comprises a poorly yielding status of the corresponding sensor element;
measuring one or more of a current and a resistance in the sensor array;
estimating a number of poorly yielding sensor elements in the sensor array based on one or more of the measured current and the measured resistance in the sensor array; and
excluding, during operation of the fault tolerant detector assembly, the poorly yielding sensor elements, wherein excluding the sensor elements comprises configuring the sensor elements to drive a signal terminal such that a signal terminal voltage is equal to a bias terminal voltage of the corresponding sensor element.

22. The method of claim 21, further comprising comparing one or more of the measured current and the measured resistance to a threshold value.

23. The method of claim 22, further comprising:
scanning the sensor array to identify the poorly yielding sensor elements in the sensor array; and
selectively programming the status indicator elements corresponding to the poorly yielding sensor elements to form a fault tolerant detector assembly.

24. A method for forming a large area detector, comprising:
forming a fault tolerant detector assembly, comprising:
providing a sensor array having a plurality of sensor elements;
providing an electronics layer having a plurality of electronics cells, wherein the plurality of electronics cells correspond to the plurality of sensor elements in the sensor array;
introducing a status indicator element in each of the plurality of the electronics cells, wherein the status indicator element is configured to store a status of a corresponding sensor element, and wherein a first value of the status comprises an operational status of the corresponding sensor element and a second value of the status comprises a poorly yielding status of the corresponding sensor element;
scanning the plurality of sensor elements in the sensor array to identify the status of the plurality of sensor elements in the sensor array;
generating a functionality map based on the identified status of the plurality of sensor elements in the sensor array;
selectively programming the status indicator elements based on the functionality map to form a fault tolerant detector assembly, wherein selectively programming the status indicator elements based on the functionality map comprises changing a status of a status indicator element from a first value to a second value based on the functionality map;
excluding, during operation of the fault tolerant detector assembly, sensor elements corresponding to electronics cells having an associated status indicator element set to the second value, wherein excluding the sensor elements comprises configuring the sensor elements to drive a signal terminal such that a signal terminal voltage is equal to a bias terminal voltage of the corresponding sensor element; and
tiling a plurality of fault tolerant detector assemblies on a support structure to form the large area detector.

25. The method of claim 24, further comprising simultaneously scanning one or more of the plurality of fault tolerant detector assemblies to identify a status of the plurality of sensor elements in each of the plurality of fault tolerant detector assemblies.

* * * * *